United States Patent
Hogan

(10) Patent No.: US 9,113,782 B2
(45) Date of Patent: Aug. 25, 2015

(54) MULTIPLE REFERENCE OCT SYSTEM

(71) Applicant: Joshua Noel Hogan, Los Altos, CA (US)

(72) Inventor: Joshua Noel Hogan, Los Altos, CA (US)

(*) Notice: Subject to any disclaimer, the term of this patent is extended or adjusted under 35 U.S.C. 154(b) by 189 days.

(21) Appl. No.: 13/907,904

(22) Filed: Jun. 1, 2013

(65) Prior Publication Data

US 2013/0322721 A1    Dec. 5, 2013

Related U.S. Application Data

(60) Provisional application No. 61/654,696, filed on Jun. 1, 2012.

(51) Int. Cl.
*G06K 9/00* (2006.01)
*A61B 5/00* (2006.01)
*A61B 3/10* (2006.01)

(52) U.S. Cl.
CPC ............... *A61B 5/0033* (2013.01); *A61B 3/102* (2013.01)

(58) Field of Classification Search
None
See application file for complete search history.

(56) References Cited

U.S. PATENT DOCUMENTS

| | | | |
|---|---|---|---|
| 2003/0233877 A1* | 12/2003 | Grez et al. | 73/579 |
| 2006/0089548 A1* | 4/2006 | Hogan | 600/316 |
| 2007/0232872 A1* | 10/2007 | Prough et al. | 600/316 |
| 2010/0150467 A1* | 6/2010 | Zhao et al. | 382/264 |

* cited by examiner

*Primary Examiner* — Amara Abdi

(57) ABSTRACT

The invention provides for generating a set of signature signals that correspond to a range of depths within a target. These signature signals can include multiple individual reference signals and be can modified to compensate for specific characteristics of the target. In the preferred embodiment the members of the set of signature signals are correlated with data sets by phase rotating individual reference signals to determine maximum and minimum correlation and thereby enabling determination of the scattering characteristic of the target at each depth. Also a pilot signal is monitored to dynamically determine the phase relationship between individual reference signals and thereby avail of phase sensitive detection techniques to enhance SNR at deeper regions where multiple individual reference signals exist.

3 Claims, 6 Drawing Sheets

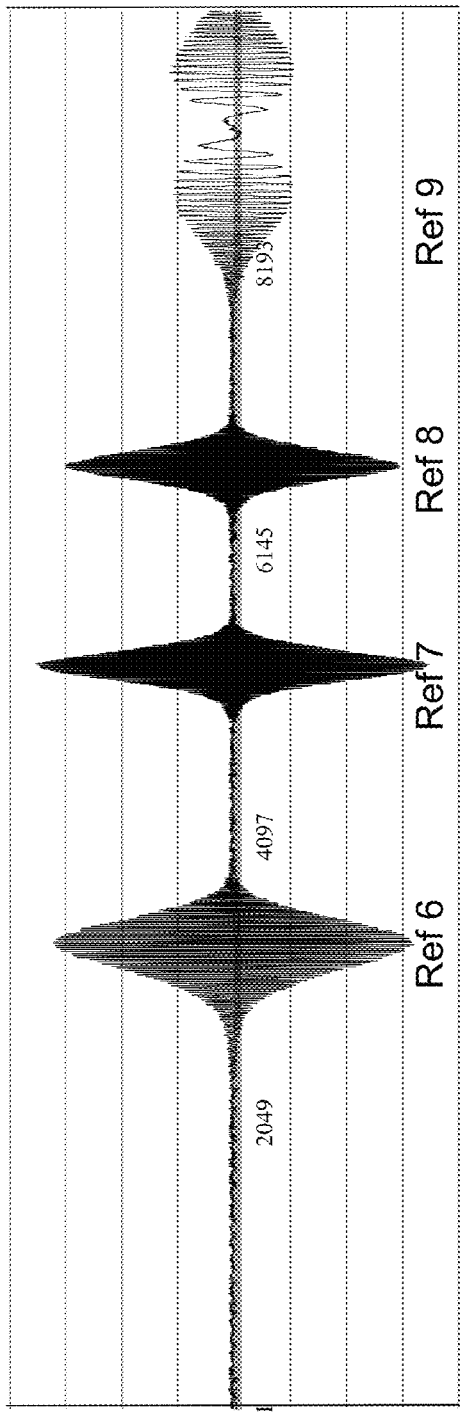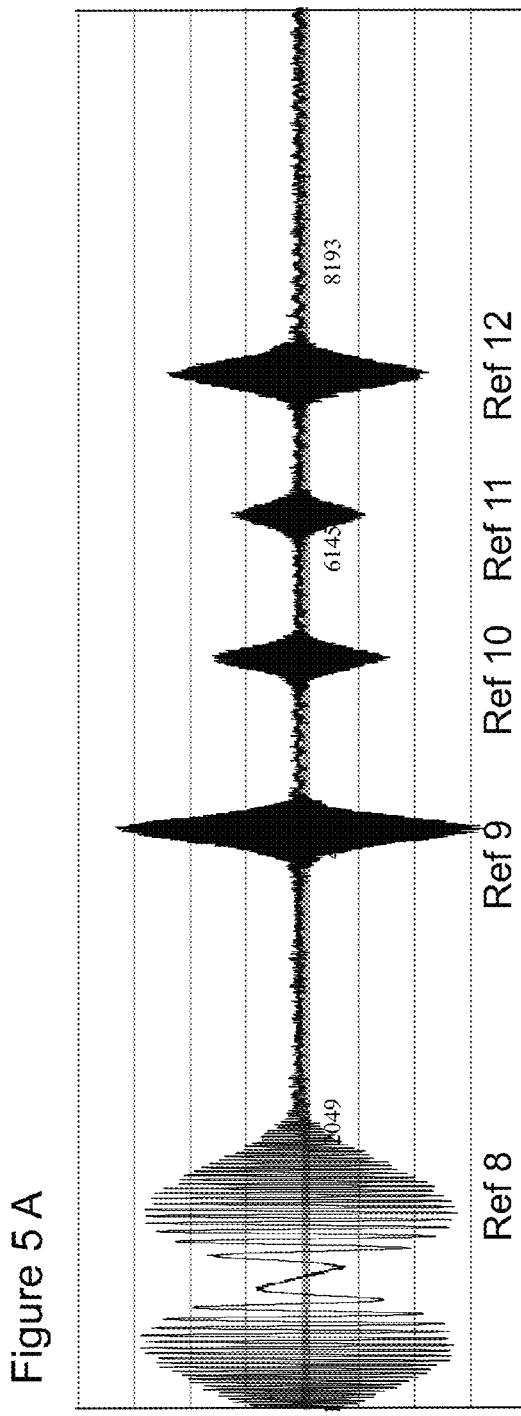
Figure 5 A
Figure 5 B

MULTIPLE REFERENCE OCT SYSTEM

CROSS REFERENCES TO RELATED PATENTS OR APPLICATIONS

This application claims priority from provisional patent application 61/654,696, and is further related to U.S. Pat. No. 7,526,329 titled Multiple reference non-invasive analysis system and U.S. Pat. No. 7,751,862 titled Frequency Resolved Imaging System, the contents of both of which are incorporated by reference as if fully set forth herein.

FIELD OF THE INVENTION

The invention described and illustrated in this application relates to non-invasive imaging and analysis techniques such as Optical Coherence Tomography (OCT). In particular it relates processing interference signals captured by OCT systems that use multiple reference signals to generate interference signals. The multiple reference OCT system is also referred to herein as an MRO system.

Such multiple reference systems include, but are not limited to, the multiple reference OCT systems described in U.S. Pat. Nos. 7,751,862 and 7,526,329 incorporated herein by reference.

BACKGROUND OF THE INVENTION

Non-invasive imaging and analysis of targets is a valuable technique for acquiring information about systems or targets without undesirable side effects, such as damaging the target or system being analyzed. In the case of analyzing living entities, such as human tissue, undesirable side effects of invasive analysis include the risk of infection along with pain and discomfort associated with the invasive process. In the case of quality control, it enables non-destructive imaging and analysis on a routine basis.

Optical coherence tomography (OCT) is a technology for non-invasive imaging and analysis. There are more than one OCT techniques. Time Domain OCT (TD-OCT) typically uses a broadband optical source with a short coherence length, such as a super-luminescent diode (SLD), to probe and analyze or image a target. Multiple Reference OCT (MRO) is a version of TD-OCT that uses multiple reference signals. Another OCT technique is Fourier Domain OCT (FD-OCT). A version of Fourier Domain OCT, called Swept Source OCT (SS-OCT), typically uses a narrow band laser optical source whose frequency (or wavelength) is swept (or varied) over a broad wavelength range. In TD-OCT systems the bandwidth of the broadband optical source determines the depth resolution. In SS-OCT systems depth the wavelength range over which the optical source is swept determines the depth resolution.

TD-OCT technology operates by applying probe radiation from the optical source to the target and interferometrically combining back-scattered probe radiation from the target with reference radiation also derived from the optical source. The typical TD-OCT technique involves splitting the output beam into probe and reference beams, typically by means of a beam-splitter, such as a pellicle, a beam-splitter cube or a fiber coupler. The probe beam is applied to the system to be analyzed (the target). Light or radiation is scattered by the target, some of which is back scattered to form a back-scattered probe beam, herein referred to as signal radiation.

The reference beam is typically reflected back to the beam-splitter by a mirror. Light scattered back from the target is combined with the reference beam, also referred to as reference radiation, by the beam-splitter to form co-propagating reference radiation and signal radiation. Because of the short coherence length only light that is scattered from a depth within the target whose optical path length is substantially equal to the path length to the reference mirror can generate a meaningful interferometric signal.

Thus the interferometric signal provides a measurement of scattering properties at a particular depth within the target. In a conventional TD-OCT system, a measurement of the scattering values at various depths can be determined by varying the magnitude of the reference path length, typically by moving the reference mirror. In this manner the scattering value as a function of depth can be determined, i.e. the target can be scanned.

There are various techniques for varying the magnitude of the reference path length. Fiber based systems use fiber stretchers, however, they have speed limitations and have size and polarization issues. Rotating diffraction gratings can run at higher speeds, however, such gratings are alignment sensitive and have size issues.

Piezo devices can achieve high speed scanning and can have high pointing accuracy, however to achieve a large scanning range requires expensive controls systems and have limited speed. A scanning method that effectively amplifies the scan range of a piezo device is described in the U.S. Pat. Nos. 7,526,329 and 7,751,862 incorporated herein. This scanning method is also applicable to electro-mechanical voice coil actuators that can have considerable scanning range.

The technique described in these incorporated references uses multiple reference signals with increasing scan range and correspondingly increasing frequency interference signals. This scanning method can achieve large scan range at high speed with good pointing stability.

The interference signals associated with the multiple references are detected by a single detector as a complex signal consisting the combined interference signals and noise of various types. Types of noise may include; optical noise in the optical source; unwanted interference signals due to reflections from surfaces of optical components; detector noise; shot noise of a photo-diode; and electronic noise.

In swept source Fourier domain OCT systems depth scanning is accomplished by repeatedly sweeping the wavelength of the optical source. The wavelength range over which the optical source is swept determines the depth resolution. The period of the sweep repetition rate determines the period of the depth scans.

In addition to depth scanning, lateral scanning is required for many imaging and analysis applications. There are many conventional techniques for lateral scanning, such as the use of stepper or linear motors. Some applications require angular scanning, which is typically accomplished by electro-mechanical oscillating mirrors, typically referred to as galvo-scanners.

In conventional TD-OCT systems the detected interference signals typically are centered about a specific frequency that is determined by the speed with which the reference path length varies and the center wavelength of the light being used, while in SS-OCT systems the detected interference signals typically are centered about a specific frequency that is determined by the speed with which the optical source is swept and the wavelength of the light being used. The interference signals are typically filtered and down converted to a baseband signal prior to digitization and further processing.

In Multiple Reference OCT (MRO), a version of TD-OCT that uses multiple reference signals, the set of detected interference signals are centered about a frequency that is determined by the speed with which the reference path length varies and the center wavelength of the light being used and integer multiples of this frequency.

An MRO system using a piezo devices as a scanning method can be operated by driving the piezo device with a constant speed for a significant portion of its scan range, referred to as the linear range. In this case the detected interference signals have constant frequencies over the linear range, i.e. the signals are linearized by ensuring the piezo is driven at constant speed.

Alternatively the MRO system can be operated by driving the piezo device with a sinusoidal (or other) waveform. In this case the detected interference signals have frequencies that vary continuously over the range of the piezo scan. The resulting digitized detected signals are typically post-processed to compensate for the varying or non-linear motion of the piezo device. The resulting "linearized" signals have constant frequencies over a significant portion of the scan range.

In both of the above MRO systems the constant frequency signals or the linearized signals are further processed by using a bank of filters with center frequencies at integer multiples of a fundamental frequency in order to separate out the information contained at the different frequencies and relating to different scan segments. This is described in more detail in the U.S. Pat. Nos. 7,526,329 and 7,751,862 incorporated herein by reference.

This processing approach has several disadvantages that negatively impact the signal to noise ratio (SNR) that the MRO system can achieve. For example: linearizing the interference signals by driving the piezo at constant speed requires the drive signal be matched to the specific piezo device (whose characteristics may change with time) and precludes using low cost transformers for voltage amplification; linearizing the interference signals by post-processing the digitized data distorts the noise characteristics of the system; crosstalk can occur between different frequencies, an issue that is exacerbated as the bandwidth of the optical source is increased; the information from different scan segments must be normalized in amplitude and aligned with each other; the SNR decreases for the higher order reference signals.

There is therefore an unmet need for a method, apparatus and system for acquiring and processing interference signals for optical coherence tomography systems, and similar such non-invasive imaging and analysis techniques and systems, that enables using low cost transformers for voltage amplification; that does not distort the noise characteristics of the system; that eliminates crosstalk especially as the bandwidth of the optical source is increased; that does not require scan segment amplitude normalization or alignment, and that maintains good SNR even for the higher order reference signals.

BRIEF SUMMARY OF THE INVENTION

The invention taught herein meets at least all of the aforementioned unmet needs. The invention provides a method, apparatus and system for acquiring and processing interference signals for optical coherence tomography systems, and similar such non-invasive imaging and analysis techniques and systems, where the invention enables using low cost transformers for voltage amplification; does not distort the noise characteristics of the system; eliminates crosstalk especially as the bandwidth of the optical source is increased; does not require scan segment amplitude normalization or alignment and maintains good SNR even for the higher order reference signals.

The invention teaches generating a set of signature signals that correspond to a range of depths within a target. These signature signals can include multiple individual reference or interference signals and be can modified to compensate for specific characteristics of the target. In the preferred embodiment, the members of the set of signature signals are correlated with data sets by phase rotating individual components of the signature signals to determine maximum and minimum correlation, thereby enabling determination the scattering characteristics of the target at each depth. A method according to the invention comprises the steps of generating a set of signature signals where each signature signal of said set of signature signals results from an interaction of reference radiation of the multiple reference OCT system and scattered probe radiation of said multiple reference OCT system where said scattered probe radiation is scattered by a scatterer at a pre-determined distance from a multiple reference OCT system where said distance is along the direction of the probe radiation;

acquiring at least one data set from a target using said multiple reference OCT system; correlating said set of signature signals with said data set to generate a set of correlation values; and outputting said set of correlation values to form a depth scan.

1. In one embodiment, a pilot signal is monitored to dynamically determine the phase relationship between individual components of the signature signals and thereby avail of phase sensitive detection techniques to enhance SNR at deeper regions where multiple individual reference or interference signals exist within a single signature signal. It should be noted that in the deeper regions where improved SNR is typically most valuable a greater number of multiple individual reference or interference signals exist within a single signature signal. An improved system according to the invention comprises a multiple reference OCT system, where the OCT system comprises a radiation source, generating reference radiation and probe radiation, a control module, a processing module, a beam splitter, an optical element, a reference mirror mounted on a translational device where said translational device moves co-linearly with the reference radiation and where said translational motion is modulated by a periodic electronic drive signal from said control module, and a detector, where said multiple reference OCT system is configured, depth scan analysis of a target said system improvement comprising:

said optical element including a first surface, said first surface partially reflecting, and a second surface, said second surface weakly reflecting, where said second surface, in combination with high order reflections between said mirror and said first partially reflecting surface generates an interference signal which is used as a pilot signal, said pilot signal monitored by said processing module to dynamically determine parameters of signature signals which, when correlated with data sets acquired by said OCT system produces at least one depth scan with improved signal to noise ratio.

BRIEF DESCRIPTION OF THE DRAWINGS

FIG. 4A illustrates a mirror interference signal centered on the first reference signal.

FIGS. 5, A and B inclusive, is an illustration of higher order reference or interference signals. FIG. 5A illustrates a set of interference signals centered on the seventh order reference signal. This figure depicts the scattering signature for this specific depth and consists of the reference or interference signal components Ref 6, Ref 7, Ref 8 and part of Ref 9. FIG. 5B illustrates a set of interference signals centered on the tenth order reference signal. This figure depicts the scattering signature for this deeper specific depth and consists of the reference signal components (part of) Ref 8, Ref 9, Ref 10, Ref 11 and Ref 12.

DETAILED DESCRIPTION OF THE PREFERRED EMBODIMENT

Figure 1:
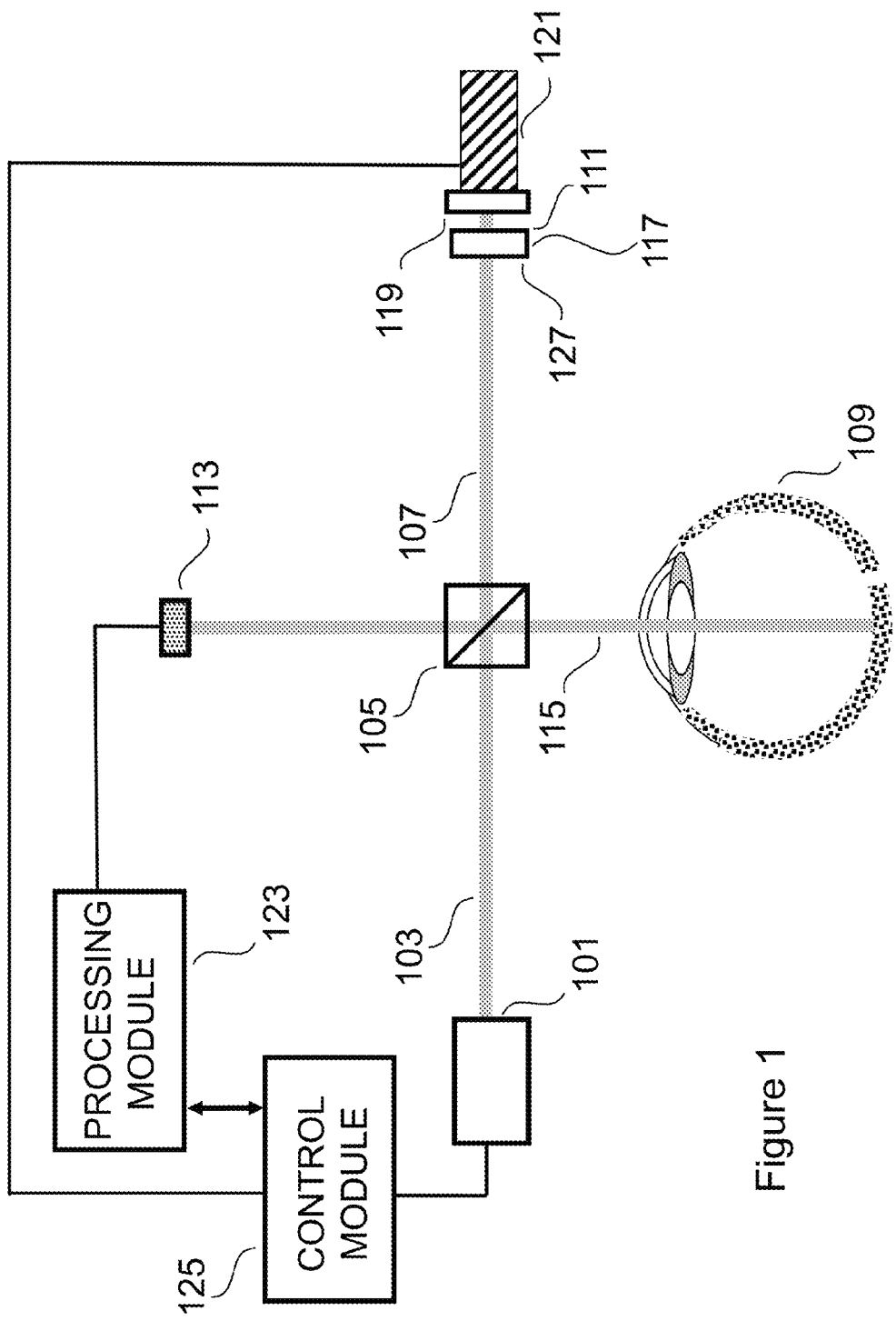
FIG. 1 is a schematic type illustration of a preferred embodiment of a multiple reference optical coherence tomography (OCT) system, also referred to as an MRO system.

The invention taught herein includes a device and method of non-invasively analyzing and imaging a target using optical radiation. The preferred embodiment includes a time domain OCT system, an example of which is included in the FIG. 1 illustration. Referring to FIG. 1, a broadband optical source 101 generates broadband output radiation 103, referred to as source radiation, that is directed at a beam-splitter 105. The beam-splitter 105 directs a component of the source radiation as initial probe radiation 115 towards a target 109 (for example the retina of an eye).

The beam-splitter 105 also transmits a component of the source radiation referred to as reference radiation 107 through an optical element 117 to a reference mirror 119 mounted on a translational device 121, such as a piezo device or an electro-mechanical translational device. The optical element 117 includes a partial mirror (or partial reflective surface) 111.

The combination of the partial mirror 111 and the reference mirror 119 mounted on a translational device 121 generate multiple reference signals, further described in U.S. Pat. No. 7,526,329 titled Multiple reference non-invasive analysis system and U.S. Pat. No. 7,751,862 titled Frequency resolved imaging system (incorporated herein by reference). The optical element 117 is a partial reflective mirror that may also include an attenuator.

In the preferred embodiment the translational device 121 is a piezo device whose length is modulated by a periodic electronic drive signal (which determines the OCT scan periodicity), however, in alternative embodiments, the translational device may be an electromechanical device, such as a voice-coil.

A portion of the reference radiation 107, modulated by the translational device 121, propagates back through the beam-splitter 105 to the detector 113 where, in combination with the back-scattered probe radiation it can generate one or more interference signals.

The interference signals are detected by at least one opto-electronic detector 113 (also referred to as a photo-diode) whose electronic output is processed by a processing module 123 in conjunction with a control module 125 that provides electronic timing signals and drive signals to the piezo device 121, and optionally to the optical source 101.

The optical element 117 includes a second surface 127 which in the preferred embodiment is a weak partial mirror (or a weakly reflecting reflective surface) 127. This second reflective surface 127, in combination with high order reflections between the mirror 119 and partial reflective surface 111 can generate an interference signal which may be used as a pilot signal.

The target 109 depicted in FIG. 1 is an eye, however, the invention is also useful for targets other than an eye. The target is not limited to biological targets, rather the invention is applicable to a broad range of targets. For example the invention is useful for document authentication, such as currency authentication or art authentication. As another example, the target may be the tissue of a finger for in-vivo generation of a three dimensional finger print.

In the invention taught herein, the multiple reference OCT system described in FIG. 1 is used to acquire data sets from one or more selected target sites. A data set consists of the data acquired over the duration of at least one full excursion of the piezo device 121 and therefore at least one full excursion of the reference mirror. Such a data set may comprise of multiple interference signals associated with the multiple reference signals corresponding to different depths within the target.

Figure 2:
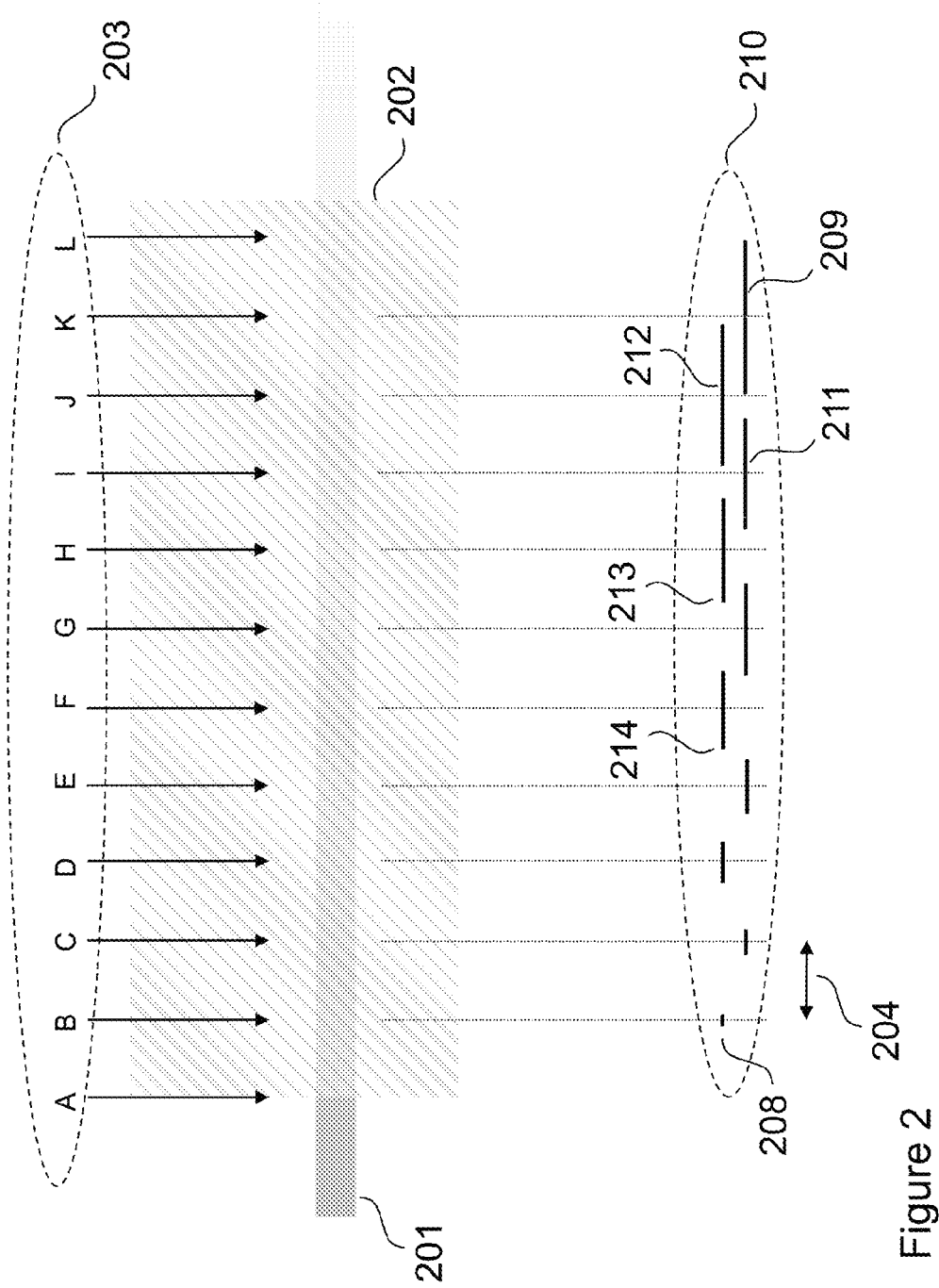
FIG. 2 is an illustration of a set of scan segments of an MRO system, including a depiction of overlapping scans.

The multiple reference OCT system is described in more detail in the U.S. Pat. Nos. 7,751,862 and 7,526,329 incorporated herein by reference. FIG. 2 illustrates an example of a set of multiple reference scan segments which depict the higher order scan segments G,H,I,J,K,L that overlap.

In order to process the acquired data sets and extract the scattering information associated with different depths, a set of signals associated with each depth from which scattering information is required. These signals associated with each depth from which scattering information is required are herein referred to as signature signals. Each of these signature signals represent the interference signal or group of interference signals that would result from an interaction of reference radiation of the multiple reference OCT system and scattered probe radiation that is scattered by a scatterer located at a particular depth within the target, i.e. at a pre-determined distance from the multiple reference OCT system, along the direction of the probe radiation.

In order to process a complete depth scan of a target, a set of signature signals would be required where the members of the set corresponded to an interference signal or group of interference signals at a number of points spanning the depth range to be scanned within the target. The separation between two successive points would be smaller than the depth resolution of the OCT system.

For example, in the case of an OCT system with a depth resolution of 10 microns (where depth resolution is determined by the bandwidth of the optical source) and where a depth range to be scanned was 1 mm, a set of 256 signature signals each separated by 4 microns would be appropriate.

Note, while it is typically desirable to have a set of signature signals on an equally spaced grid, it can be useful to have un-equal spacing in some applications. For example, if some regions of the target are of less interest, sparsely spaced points may enable more optimal use of processing cycles. A critical aspect of the signature signals is that signals associated with different points in depth are different from each other.

Signature signals could be generated by replacing the target with a mirror and systematically moving the mirror away from the OCT system in steps of, for example, 4 microns.

Figure 4:
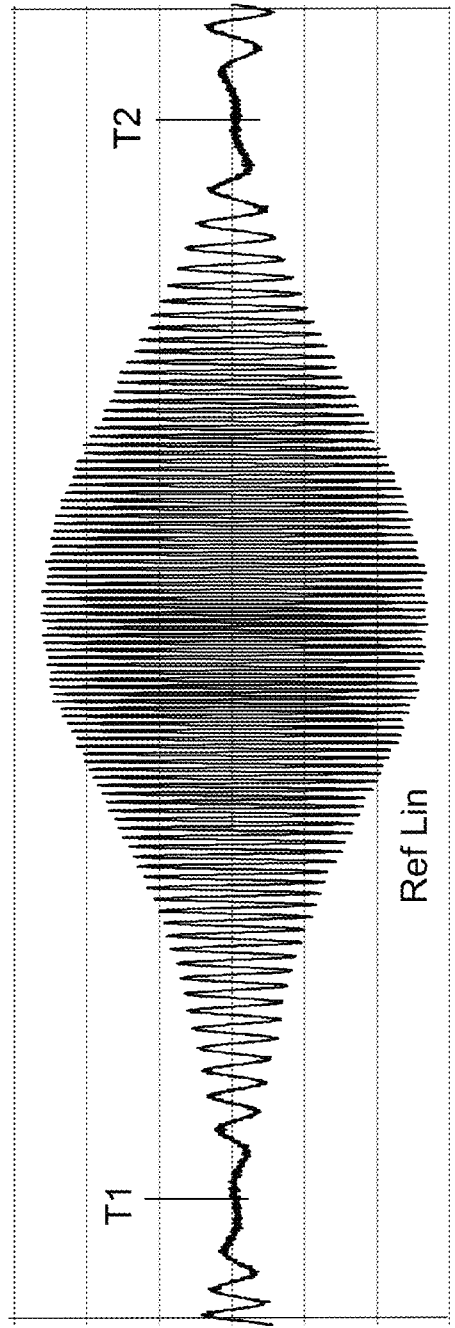
FIGS. 4A and B inclusive, is an illustration of interference signals generated by the MRO system using a mirror as a target.
FIG. 4B illustrates a mirror interference signal with the bandwidth of the SLD reduced so that the interference signal spans the range of the piezo scan. The waveform depicted in FIG. 4B can be used to determine the motion of the piezo device either by determining the separation between the zero crossings or by fitting a sine wave (with a Gaussian type envelope) to the wave form. The resulting sine wave can be used as the basis for generating synthetic signature signals at this fundamental or first order signal as well as synthetic signature signals at multiple integer times the frequency of the fundamental or first order signal. The synthetic signature signals can be further refined by fitting to actual mirror based reference signals, such as that depicted in FIG. 4A.
Figure 4:
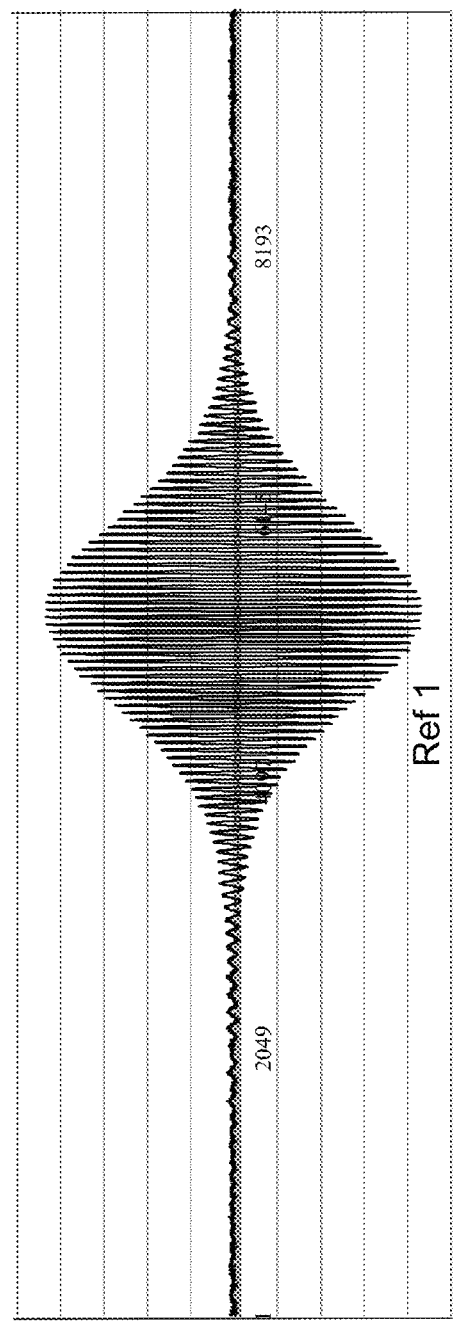

Such a signature signal, labeled Ref 1 is illustrated in FIG. 4A. The Ref 1 signal consists of a sine wave whose frequency increases from a low (or zero) value to a maximum and then decreases to a low (or zero) value. This frequency variation corresponds to the piezo device driven by a sine wave drive signal. The piezo goes from being stationary to an increasingly rapid motion and then slows down to be once again stationary, momentarily, at its extreme extension.

This piezo motion is more clearly depicted in FIG. 4B where the bandwidth of the SLD 101 has been reduced so the interference signal (labeled Ref Lin) spans the full range of the piezo motion. The "turn around" points of the piezo device (where it is stationary) are labeled T1 and T2.

As the target mirror generating the signature signals is moved further away from the OCT system, higher order interference signals are generated. For example FIG. 5A depicts the seventh order interference signal, labeled Ref 7 in the center of the trace. However because the scan segment magnitude of these high order scan segments is so large, interference signals associated with other interference signals, i.e. Ref 6, Ref 8, and Ref 9 also exist in this trace.

Another example of a signature signal consisting of multiple interference signals associated with a particular depth is illustrated in FIG. 5B where that mirror is positioned at a depth that has the tenth interference signal centered, but also has Ref 8, Ref 9, Ref 11 and Ref 12 at specific locations in the trace.

The complex "composite" interference signals illustrated in FIGS. 5A and 5B are examples of a signature signal associated with the scattering by a scatterer at a specific depth. By correlating the signature signal of a specific depth with the composite interference signal acquired by a multiple reference OCT system from a target site (e.g. a location on the retina of an eye), the scattering intensity value from that specific depth may be determined.

By correlating a set of signature signals corresponding to a set of depths within the target with the composite interference signal acquired by a multiple reference OCT system from a target site (e.g. a location on the retina of an eye), the set of depth scattering intensity values may be determined, i.e. a depth scan may be generated.

Such depth scans may be further processed by conventional averaging, peak detection or other techniques to extract, for example, biometric measurements such as layer thicknesses. Measurements, such as retinal nerve fiber layer (RNFL) thickness or central macular thickness (CMT) are valuable in monitoring or diagnosing eye diseases. An array of adjacent depth scans can be displayed as 2 or 3 dimensional images.

The invention provides for correlating a signature signal with a composite interference signal, referred to herein as a data signal, acquired by a multiple reference OCT system from a target site. Correlation may be accomplished by the following: (a) removing the DC component from both signals; (b) multiplying the signature signal and the data signal on a point by point basis to generate a first correlation value; (c) rotating the phase of the signature signal and repeating step "b" to find a second correlation value; (d) repeating step "c" until the signature signal has been rotated through 360 degrees; (e) determining the maximum and minimum correlation value; (f) outputting a final correlation value that is the difference between the maximum and minimum correlation value.

The correlation process is repeated for all of the different signature signals, each corresponding to a different depth within the target. Typically, but not necessarily, the signature signals are processed in the same order as they would be acquired by systematically stepping a reference mirror away (or towards) the OCT system. The resulting set of final correlation values represents a scattering profile or depth scan of the selected target site or sites.

The correlation process may be repeated multiple times on data sets acquired at substantially the same target site to generate multiple final valuation values, which may then be averaged or otherwise processed. Alternatively, or additionally, the correlation process may be repeated at an array of adjacent target sites and the resulting depth scans may displayed as 2 or 3 dimensional images.

In the case of using signature signals that are generated by using a mirror as the OCT target, rotating the phase may be accomplished by shifting the signature signals with respect to a data set. In circumstances, such as shown in FIGS. 5A and 5B, where there are more than one "Ref" (or multiple reference component), then the maximum and minimum of each "Ref" may be determined independently and a final correlation value computed using the maximum and minimum of each "Ref", for example by multiplying the intermediate correlation values (for each "Ref") together.

Figure 3:
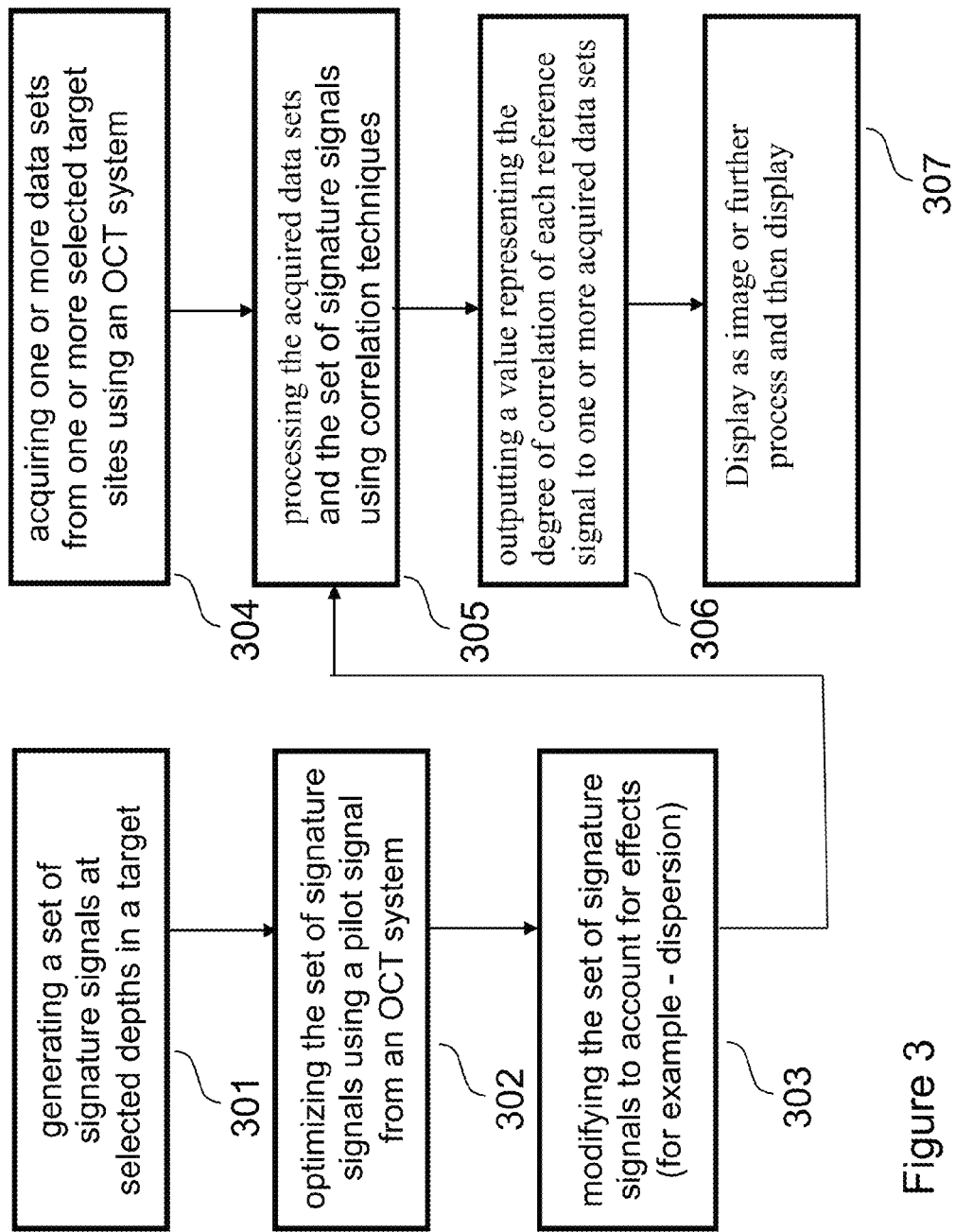
FIG. 3 is a flowchart illustrating processing steps involving correlating signature signals with data sets acquired by an MRO system.

Referring now to FIG. 3 the inventive method provides for generating a set of signature signals at selected depths in a target 301. In the preferred embodiment, the signature signals are generated synthetically based on parameters of the OCT system. Relevant parameters that determine the signature signals include: the center wavelength of the SLD; the bandwidth of the SLD; the spectral shape of the SLD; the spacing or distance between the reference mirror 119 of FIG. 1 and the partial reflective surface 111 of FIG. 1 and the reflectivity of the partial mirror 111 of FIG. 1; dispersive properties of the target; polarization properties of the target.

In the preferred embodiment, the resulting signature signals from step 301 are optimized using a pilot signal from an OCT system 302. Aspects of the signature signals may be optimized by fitting the synthetic signature signals to actual interference signals generated using a mirror. For example, the shape of the envelopes of the various synthetic signature signals may be determined by fitting to actual signals.

In the preferred embodiment, other parameters of the synthetic signature signals are dynamically determined. Such dynamically determined parameters include: the spacing or distance between the reference mirror 119 of FIG. 1 and the partial reflective surface 111 of FIG. 1; and a parameter involving the relative magnitude of various interference signal components (determined in at least part by the reflectivity of the partial mirror 111 of FIG. 1).

These parameters may be determined dynamically by monitoring a pilot signal generated by the second reflective surface 127 which in the preferred embodiment is a weak partial mirror (or a weakly reflecting reflective surface) 127 of FIG. 1. This second reflective surface 127, in combination with high order reflections between the mirror 119 and partial reflective surface 111 can generate an interference signal with multiple high order reference signals.

By choosing the optical thickness of the optical element 117 of FIG. 1 appropriately, the multiple interference signal components of the pilot signal generated due to the reflective surface 127 can be higher in frequency than the reference signals used to analyze the target. For example, the pilot signal could be centered about the twentieth reference signal. This pilot signal would also contain interference signal components above and below the twentieth interference signal (similar to the signal in FIG. 5B, which is centered on Ref 10 but also includes components above (Ref 11 and Ref 12) and below (Ref 8 and Ref 9).

The relative amplitudes of the interference signal components in the pilot signal provide the information to determine the relative amplitude of all the components of the synthetic signature signals.

The relative locations of the peaks of the envelopes of the reference signal components in the pilot signal provide the information to determine the piezo mirror and partial reflective surface spacing or the distance between the reference mirror 119 of FIG. 1 and the partial reflective surface 111 of FIG. 1 and hence the relative location of the peaks of the envelopes of the interference signal components of the synthetic signature signal components.

The relative phases of the interference signal components in the pilot signal provide the information to determine the relative phases of all the components of the synthetic signature signals. This dynamic phase information enables rotating the phases of all the signature signal components of a synthetic signature signal in unison even though they rotate at different rates where the different rates are determined by the order of the components. Rotating the phases of all the signature signal components of a synthetic signature signal in unison enables determining the correlation maximum and minimum of the complete synthetic signature signal in a phase sensitive manner.

Thus the use of the pilot signal can provide the information to optimize the set of signature signals dynamically. This enables automatically adjusting to OCT system variations such as changes in the relative amplitudes of the multiple reference interference signals or changes in the spacing or distance between the reference mirror 119 of FIG. 1 and the partial reflective surface 111 of FIG. 1. Such changes could occur due to, for example, temperature variations.

Since the relative phases of the various reference interference signals is very sensitive to changes in the spacing or distance between the reference mirror 119 of FIG. 1 and the partial reflective surface 111 of FIG. 1, having a pilot signal that dynamically provides such phase information enables phase sensitive processing which provides the opportunity for more accurately extracting signal from noise and thereby increasing the signal to noise (SNR) of the system.

An advantage of this inventive approach is that the increased signal to noise—and hence increased sensitivity—occurs at the higher order reference or interference signals where there are more frequency components present. This typically corresponds to the deeper regions of the target where signals are weaker and where increased sensitivity is most valuable.

Another advantage of this inventive approach is that there are no adverse cross-talk issues to deal with as the bandwidth of the SLD is increased (and hence resolution of the OCT system is improved), unlike conventional filter based processing.

Yet another advantage of this inventive approach is that there is no "stitching" of or combining of overlapping scan segments required as is the case with conventional filter based processing.

A further advantage of this inventive approach is that there is no requirement to "linearize" the data. Linearizing data inevitably introduces additional noise artifacts, including distorting the spectral distribution of the noise. The non-linear behavior of the piezo can be fully accounted for in the variation of the frequency of the underlying sine wave on which the synthetic (or those acquired using a mirror as a target) signature signals are based.

Yet another advantage of this inventive approach is that issues that would typically cause problems in conventional filter based processing, such as the non-linear behavior of the piezo device or a non-Gaussian spectral profile of the SLD are not problematic. On the contrary, they render the nature of the synthetic signature signals more complex and therefore less likely to be generated by a noise source.

Referring again to FIG. 3, the optimized signals are modified for effects of the target on the optical signals 303. In the preferred embodiment, the synthetically generated set of signature signals may also be modified to compensate for distorting aspects in the target. Such distorting aspects include, but are not limited to, chromatic or polarization dispersion. By adjusting the spectral profile, the synthetic signature signals can be modified to compensate for a pre-determined amount of dispersion. The aspects of a target that distort the interference signals acquired from a target by an OCT system are herein referred to as distorting characteristics of the target.

Alternatively, or in addition, the amount of dispersion can be determined and then compensated for by systematically scanning through various amounts of distortion and determining the actual amount of dispersion based on, for example, sharpness of image, or how well layers are defined.

Using one or more acquired data sets from one or more selected target sites 304, the acquired data sets are processed with respect to the set of signature signals by applying correlation techniques 305. The preferred correlation techniques have been set-forth previously herein. To briefly re-iterate, the signature signals are systematically rotated and cross-correlated with the acquired data sets so as to determine the scattering amplitude or intensity at each depth.

After performing cross-correlation a value representing the degree of correlation of each reference signal with respect to one or more data sets is output 306. From such output an image may be displayed or further processing performed prior to output 307.

In the preferred embodiment the phases of the signature signal components are determined from the pilot signal. In an alternative embodiment the relative phase of two of the components of a signature signal could be determined by independently computing the phases at which their respective correlation value were maximum and minimum and using this relative phase information to determine the "correct" relative phase of a third signature signal component.

In the preferred embodiment the relative amplitudes of the synthetic signature signal components are adjusted to produce a depth scan with a "normalized" amplitude profile, where a "normalized" amplitude profile would be a constant amplitude in the case of a mirror being used as the target. In an alternative embodiment the computed depth scan could be normalized based on a practical measurement of the interference signals acquired when using a mirror as the target.

Many alternative implementations of this invention are possible. For example, in the preferred embodiment the pilot signal is detected by the same detector 113 of FIG. 1 that detects the data interference signals from the target. In an alternative embodiment the pilot signal could be "picked off" and detected by an additional detector.

Figure 6:
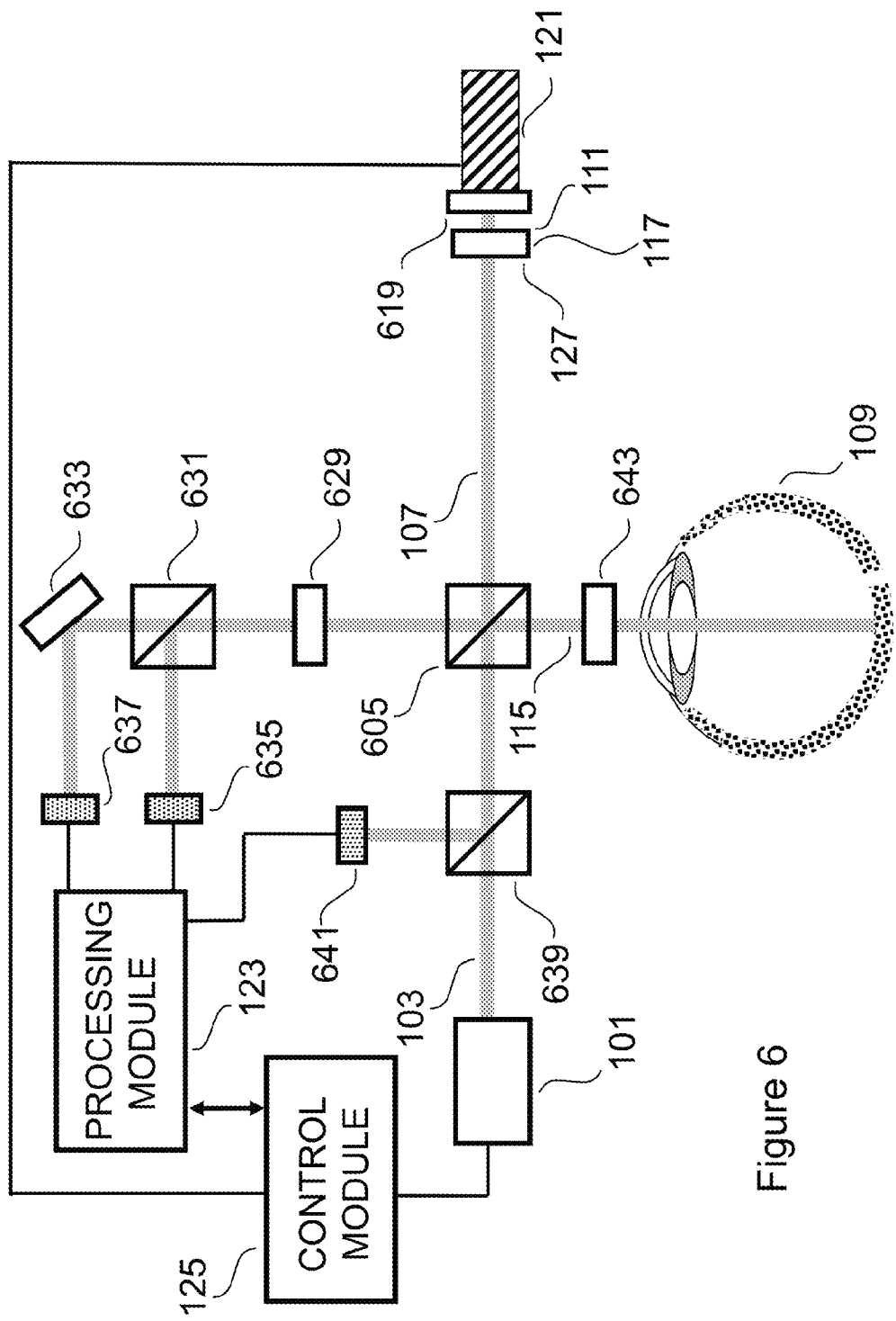
FIG. 6 is a schematic type illustration of an alternate embodiment of a polarization based multiple reference optical coherence tomography (OCT) system, (also referred to as an MRO system) that includes: a polarization rotating mirror to optimize only useful reference light reaching the detection system; balanced detection; and detection of a pilot signal.

An alternative embodiment in which the pilot signal could be "picked off" and detected by an additional detector is depicted in FIG. 6. The alternative embodiment depicted in FIG. 6 is in many respects similar to the embodiment depicted in FIG. 1, however, the beam splitter 605 is a polarized beam splitter orientated with respect to the strong polarization vector of the optical source to direct an appropriate amount of optical radiation to the target and to the reference mirror 619. In this embodiment the probe radiation 115 is directed through a quarter wave plate 643 to the target.

The quarter wave plate 643 is rotated to maximize the scattered probe radiation that is scattered back through the quarter wave plate 643 and has a polarization vector that maximizes its transmission through the beam splitter 605 towards the detection system.

In this embodiment the reference mirror 619 rotates the polarization vector of the multiple reference radiation so that at least some of the radiation reflected from the reference mirror 619 is directed by the beam splitter 605 towards the detection system while substantially all the radiation reflected by the partial reflective surface 111 (whose polarization vector is not rotated) is transmitted straight through the beam splitter 605 and not towards the detection system.

The co-propagating but orthogonally polarized scattered probe and reference radiation pass through an optional half wave plate to a second polarized beam splitter 631 which directs one polarization component of the scattered probe and reference radiation to a first detector 635 and transmits the other polarization component to a turning mirror 633 which directs the second component of the scattered probe and reference radiation to a second detector 637.

The output of the two detectors 635 and 637—which are typically photo-detectors—are made available to the processing module 123 for balanced detection, thereby reducing common mode noise, and further signal processing including correlation with the set of signature signals.

A portion of the reference radiation passing through the polarized beam splitter 605 is directed by another beam splitter (or pick off optic) towards a third detector 641 (typically a photo-diode) and made available to the processing module 123 for extraction of the pilot signal that is comprised of a group on interference signal that are generated by the interaction between the radiation reflected by the weakly reflective surface 127 (back to the partial mirror 111) and (high order) radiation reflected by the reference mirror 119.

The pilot signal is used by the processing module 123 to dynamically configure synthetic signature signals and thereby optimize correlation of the signature signals with data sets captured from the target. An advantage of the use of balanced detection is that the pilot signal will appear as a common mode signal that will not interfere with the data signal and therefore can be at a lower frequency, thus reducing the bandwidth requirements of the detection system.

An advantage of not having substantially all the radiation reflected by the partial reflective surface 111 (whose polarization vector is not rotated) is transmitted straight through the beam splitter 605 and not towards the detection system is reduced shot noise and the opportunity to increase the reflectivity of the partial mirror 111 from a typical value of the order of 80% in the non-polarized preferred embodiment to a reflectivity of the order of 92% in the case of the polarized system. Increasing this reflectivity reduces the rate at which the amplitude of reflections decrease.

Many variations of the above embodiments are possible. For example the pilot signal could be generated from an appropriately positioned reflective surface other than the one described above. The invention described could be combined with a conventional filtering based approach. For example lower order interference signals could be processed in a conventional manner while higher order overlapping interference signals could be processed by the method described herein.

Other examples will be apparent to persons skilled in the art. The scope of this invention should be determined with reference to the specification, the drawings and the appended claims, along with the full scope of equivalents as applied thereto.

What is claimed is:

1. A method of analyzing a target wherein said method includes the steps of:

generating a set of signature signals where each signature signal of said set of signature signals results from an interaction of reference radiation of a multiple reference optical coherence tomography system and scattered probe radiation of said multiple reference optical coherence tomography system where said scattered probe radiation is scattered by a scatterer at a pre-determined distance from a multiple reference optical coherence tomography system where said distance is along the direction of the probe radiation;

acquiring at least one data set from a target using said multiple reference optical coherence tomography system;

correlating said set of signature signals with said data set to generate a set of correlation values, wherein the step of correlating said set of signature signals with said data set to generate a set of correlation values includes the sub-step of rotating the phase of at least some of the components of said signature signals, and computing a difference between a maximum and minimum correlation value to generate a set of final correlation values resulting in a depth scan with an improved signal to noise ratio; and outputting said set of correlation values to form a depth scan.

2. The method of claim 1, wherein the sub-step of rotating the phase of at least some of the components of said signature signals uses information derived from a pilot signal.

3. The method of claim 1, wherein the step of correlating said set of signature signals with said data set to generate a set of correlation values includes the sub-step of shifting at least some components of the reference signals in order to rotate the phase of at least some of said reference signals, and computing a difference between a maximum and minimum correlation value to generate a set of final correlation values resulting in a depth scan with an improved signal to noise ratio.

* * * * *